(12) United States Patent
Knigge

(10) Patent No.: US 6,482,401 B1
(45) Date of Patent: Nov. 19, 2002

(54) COMPOSITION FOR THE RELIEF OF JOINT PAIN AND MYOFASCIAL PAIN AND METHOD OF PREPARING SAME

(75) Inventor: Jan Donald Knigge, St. Petersburg, FL (US)

(73) Assignee: Naturopathic Laboratories International, Inc., Great Neck, NY (US)

( * ) Notice: Subject to any disclaimer, the term of this patent is extended or adjusted under 35 U.S.C. 154(b) by 0 days.

(21) Appl. No.: 09/410,868

(22) Filed: Oct. 1, 1999

Related U.S. Application Data

(62) Division of application No. 09/219,412, filed on Dec. 23, 1998, now abandoned.

(51) Int. Cl.[7] ............... A61K 31/726; A61K 31/737
(52) U.S. Cl. ............... 424/78.05; 424/401; 514/54; 514/62; 536/55.1; 536/55.2
(58) Field of Search ............... 514/62, 54; 424/401, 424/78.02, 78.03, 78.05; 536/55.2, 55.1

(56) References Cited

U.S. PATENT DOCUMENTS

| | | | | |
|---|---|---|---|---|
| 4,473,551 A | * | 9/1984 | Schinitsky | 424/95 |
| 4,702,916 A | | 10/1987 | Geria | 424/400 |
| 5,178,881 A | * | 1/1993 | Mackles et al. | 424/489 |
| 5,326,357 A | | 7/1994 | Kandel | 623/16 |
| 5,364,845 A | | 11/1994 | Henderson | 514/54 |
| 5,587,363 A | | 12/1996 | Henderson | 514/54 |
| 5,639,740 A | | 6/1997 | Crandall | 364/140 |
| 5,804,594 A | | 9/1998 | Murad | 514/474 |
| 5,840,715 A | | 11/1998 | Florio | 514/62 |
| 5,877,212 A | * | 3/1999 | Yu et al. | 514/557 |

OTHER PUBLICATIONS

File Promt on STN. An No. 97:562409. 'Born Again Glucosamin Pain Relieving Roll On with Capsaicin and Chondoritin; Glucosamine Pain Relieving Creme with Capsaicin'. Product Alert (Oct. 13, 1997) Issn: 0740–3801. (abstract only).*

* cited by examiner

*Primary Examiner*—Christopher S. F. Low
*Assistant Examiner*—Anish Gupta
(74) *Attorney, Agent, or Firm*—Bryan Cave LLP

(57) ABSTRACT

A stable, formulation comprising glucosamine and chondroitin compounds in a base mixture which can be used for topical application to relieve joint pain and myofascial pain. A method of preparing the composition by adding the glucosamine and chondroitin after the rest of the components of the formulation have been mixed and heated is also disclosed.

8 Claims, No Drawings

COMPOSITION FOR THE RELIEF OF JOINT PAIN AND MYOFASCIAL PAIN AND METHOD OF PREPARING SAME

This is a division, of U.S. application Ser. No. 09/219,412 filed Dec. 23, 1998, now abandoned.

FIELD OF INVENTION

This invention relates to a topically applied composition for the treatment of joint pain and myofascial pain, a process for preparing the composition, and a method of treating joint pain and myofascial pain using the composition.

BACKGROUND OF THE INVENTION

Joint pain and myofascial pain can be caused by arthritis, cartilage injury or disease, and other sources. Patients can find such pain to be debilitating, and have used a variety of treatments for relief of pain, including formulations administered orally, parenterally, and topically. A popular form of treatment for joint pain and myofascial pain is the topical application of pain relieving ointments which contain menthol.

Formulations for topical application can either be water-based or substantially anhydrous. For many applications, anhydrous (i.e. oil-based) formulations are preferable because anhydrous formulations will not evaporate like those containing water or alcohol. Anhydrous formulations, therefore, are easier to use in massaging applications.

The use of chondroitin and glucosamine in the repair of connective tissue is well known. For example, U.S. Pat. Nos. 5,587,363 and 5,364,845 describe the use of a mixture of glucosamine and chondroitin in an oral formulation for the repair of connective tissue.

The use of glucosamine and chondroitin in topical formulations is also known. However, it was not known to use them together in a substantially anhydrous base mixture. In fact, until now, it has not been possible to prepare a stable, substantially anhydrous, topical formulation containing both a chondroitin and a glucosamine. Moreover, it was not known to use glucosamine and chondroitin in combination with an analgesic in a formulation for topical application.

SUMMARY OF THE INVENTION

One object of this invention is to provide an stable, topical composition for the temporary treatment of joint pain and myofascial pain.

A further object of this invention is to provide an improved method for the temporary treatment of joint pain and myofascial pain.

A further object of this invention is to provide a method for preparing a stable, topical formulation for the temporary treatment of joint pain and myofascial pain comprising chondroitin and glucosamine.

These and other objects are achieved by a topical formulation comprising a glucosamine compound and a chondroitin compound in an anhydrous base mixture, wherein the formulation is stable, as defined below, for ten days or more.

A further object of this invention is a topical formulation comprising a glucosamine compound and a chondroitin compound in combination with an analgesic.

DETAILED DESCRIPTION OF THE INVENTION

As used in this specification, the term "chondroitin" means a compound selected from chondroitin, chondroitin salts, and mixtures thereof, and glucosamine means a compound selected from the group consisting of glucosamine, glucosamine salts and mixtures thereof. The preferred species of glucosamine is glucosamine sulfate, while the preferred species of chondroitin is chondroitin sulfate.

By "stable," what is meant is that the formulation, when stored at a temperature of 104° F. at a relative humidity of 75%, remains uniformly mixed, so that none of the components separates from the rest of the formulation. Thus, the overall composition remains unchanged and, the glucosamine and chondroitin are evenly distributed throughout the formulation. The compositions according to the invention are stable for at least 10 days, preferably are stable for at least 30 days, and most preferably are stable for at least 60 days. Ideally, the composition is stable for at least 90 days.

By "substantially anhydrous," what is meant is that the total water content of the formulation is not more than 0.2% by weight. As used in this application, the term "base mixture" means a mixture of all of the components of the formulation of the invention except for the chondroitin and the glucosamine. Unless otherwise noted, all percentages are by weight relative to the total weight of the formulation.

The base mixture, is preferably substantially anhydrous, but may otherwise comprise those materials commonly used by those of ordinary skill in the art of preparing topical formulations. For example, anhydrous lanolin, copaiba oil, lavender oil, citrus oil, eucalyptus oil, and cannola oil, and other materials can be used to make up the anhydrous base mixture. Pain relieving materials, such as menthol, capsaicin, and methyyl salicylate may also be used in the base mixture. In addition, the base mixture can include colorants, fragrances, and preservatives, as will be known to those of ordinary skill in this art.

Generally, the total amount of the base mixture material will range from about 70% to about 99.9% by weight. Preferably, the total amount will be from about 97% to 99% by weight. Preferably, the formulation will also include a pain relieving material, in amounts from about 3% to about 25% by weight, preferably from about 10% to about 20% by weight, most preferably about 16% by weight. As noted above, the base mixture can include preservatives and coloring agents. Generally the total amount of such additives would not exceed 5% by weight of the total formulation. However, the base mixture preferably does not contain such additives.

In a preferred embodiment, the topical formulation according to the invention comprises anhydrous lanolin, menthol, eucalyptus oil, citrus oil, copaiba oil, and lavender oil, as well as chondroitin sulfate and glucosamine sulfate.

Glucosamine and chondroitin are each present in amounts from about 0.01% to about 3% by weight. Preferably, the glucosamine and chondroitin are each present in amounts from about 0.05% to about 2% by weight. Most preferably glucosamine and chondroitin are each present in amounts from about 0.1% to about 1.5% by weight.

It has been found that the combination of anhydrous lanolin with chondroitin and glucosamine produces unexpected results in effectuating the penetration of the pain relieving agent, such as menthol, into the skin. The combination of lanolin, chondroitin and glucosamine has also been found to have unexpectedly good moisturizing effects on the skin. Moreover, the compositions according to the invention, which include both glucosamine and chondroitin, are smoother and are superior emollients than similar formulations without the glucosamine and the chondroitin.

A further embodiment of the invention is a topical formulation comprising an analgesic, chondroitin, and glucosamine. In this embodiment of the invention, the base mixture need not be substantially anhydrous. Such a topical formulation is novel and provides increased benefits with respect to the penetration and effectiveness of the analgesic as compared with prior art topical formulations.

The inventors have found a novel method of preparing the formulation of the invention. Specifically, the components of the base mixture are mixed together in conventional fashion, for example by using a medium speed agitator. This base mixture is then heated to a temperature of about 120° F. to about 160° F., preferably from about 130° F. to about 150° F., most preferably about 140° F. Generally, the mixture is kept at this elevated temperature for about 1 to about 2 hours, though it can be for a different amount of time. The mixture is then allowed to cool to a temperature of about 50° F. to about 90° F., preferably from about 60° F. to about 80° F., most preferably about 72° F. The mixture is allowed to stand at this temperature for a period of at least 2 hours, more preferably at least 8 hours, and most preferably at least 12 hours. Ideally, the mixture will be allowed to stand for about 24 hours.

Following the waiting period, the chondroitin and glucosamine are mixed in. This mixing can be accomplished using a medium speed agitator. The mixing in of the chondroitin and the glucosamine continues for a period of about 1 to about 10 hours, preferably for about 2 hours. The mixing must continue for at least as long as is necessary to achieve a uniform distribution of the glucosamine and the chondroitin in the formulation. The formulation is then allowed to stand for at least 1 hour, preferably for at least 3 hours, and most preferably for at least 4 hours. The formulation is then mixed for an additional period of about 1 to about 10 hours, preferably for about 2 hours.

Another embodiment of this invention is a method for treating joint pain and/or myofascial pain comprising the application of an effective amount of the anhydrous formulation described above to the area of the skin overlying the painful joint or soft tissue.

I claim:

1. A process for preparing a substantially anhydrous topical formulation comprising a base mixture, chondroitin, and glucosamine, the formulation being stable for at least 10 days, the process comprising the following steps:

(a) mixing components of the base mixture, and heating the base mixture to a temperature of about 120° F. to 160° F.;

(b) letting the base mixture from step (a) stand for a period of at least two hours at a temperature of about 50° F. to 90° F.; and (c) mixing the chondroitin and the glucosamine into the base mixture from step (b) to obtain a substantially anhydrous topical formulation.

2. The process according to claim 1, wherein the mixture from step (c) is allowed to stand for a period of at least 1 hour, followed by additional mixing.

3. The process according to claim 1, wherein the mixing of step (a) occurs at a temperature of about 130° F. to 150° F.

4. The process according to claim 3, wherein the mixing of step (a) occurs at a temperature of about 140° F.

5. The process according to claim 1, wherein step (b) occurs at a temperature of about 60° F. to 80° F.

6. The process according to claim 1, wherein, the base mixture in step (b) is allowed to stand for at least 8 hours.

7. The process according to claim 6, wherein, the base mixture in step (b) is allowed to stand for at least 12 hours.

8. The process according to claim 2, wherein the mixture from step (c) is allowed to stand for about 2 hours, followed by about 2 hours of additional mixing.

* * * * *